US005702422A

United States Patent [19]
Stone

[11] Patent Number: 5,702,422
[45] Date of Patent: Dec. 30, 1997

[54] ANTERIOR CRUCIATE LIGAMENT REPAIR METHOD

[76] Inventor: Kevin R. Stone, 1 Throckmorton La., Mill Valley, Calif. 94941

[21] Appl. No.: 567,895

[22] Filed: Dec. 6, 1995

[51] Int. Cl.$^6$ ................................................. A61B 17/00
[52] U.S. Cl. .............................. 606/232; 606/73; 606/80
[58] Field of Search .................................. 606/1, 72, 73, 606/75, 76, 232, 80, 86, 88, 102, 96, 66; 128/897, 898; 623/13

[56] References Cited

U.S. PATENT DOCUMENTS

| | | |
|---|---|---|
| 4,632,100 | 12/1986 | Somers et al. |
| 5,139,520 | 8/1992 | Rosenberg ............................. 606/102 |
| 5,370,662 | 12/1994 | Stone et al. |
| 5,372,599 | 12/1994 | Martins ................................... 606/75 |
| 5,374,269 | 12/1994 | Rosenberg ............................. 606/80 |
| 5,505,735 | 4/1996 | Li ............................................ 606/72 |

OTHER PUBLICATIONS

Marshall, John L. et al., (1979), *Clin. Orthop. Rel. Res.*, 143, 97–106.
Gollehon et al., (1985), *Orthop. Clin. North Am.*, 16, 111–124.
Feagin, John A., Jr., (1979), *Orthop. Clin. North Am.*, 10, 80–90.
Feagin, et al., (1976), *Am. J. Sports Med.*, 4, 95–100.
Higgins, et al., (1987), *Am. J. Sports Med.*, 15, 439–447.
Sherman, et al., (1991), *Am. J. Sports Med.*, 19, 243–255.
Kaplan, et al., (1990), *Am. J. Sports Med*, 18, 354–358.
Straub, et al., (1986), *Clin. Orth. and Related Research*, 227, 238–250.
Sommerlath, et al., (1991), *Am. Journal of Sports Med.*, 19, 156–162.
Amiel, et al., (1989), *Journal Orthop. Res.*, 7, 486–493.
Kohn, D., (1986), *Arthroscopy*, 2, 98–102.
Lazovic, Djordje et al., (1993) *Acta Orthop. Scand.*, 64, 583–586.

*Primary Examiner*—William Lewis
*Attorney, Agent, or Firm*—Lappin & Kusmer LLP

[57] ABSTRACT

The invention provides a method of repairing tears or ruptures in an anterior cruciate ligament of the human knee, by reattaching the ligament to its anatomic insertion site on the intercondylar notch of the femur using a suture anchor, with healing at the insertion site being enhanced by formation of a cancellous bleeding bed.

15 Claims, 3 Drawing Sheets

ANTERIOR CRUCIATE LIGAMENT REPAIR METHOD

The present invention relates to the field of surgical repair of injuries of the anterior cruciate ligament in the human knee.

BACKGROUND OF THE INVENTION

The anterior cruciate ligament of the knee (hereinafter the ACL), schematically depicted in FIG. 1, functions to resist anterior displacement of the tibia 10 from the femur 20 at all flexion positions. The ACL also resists hyperextension and contributes to rotational stability of the fully extended knee during internal and external tibial rotation. The ACL may play a role in proprioception. Structurally, the ACL attaches to a depression in the front of the intercondylar eminence of the tibia (the tibial insertion site 12), extending from the anterior horn of the lateral meniscus 30. The ACL extends upward, backward, and laterally, through the intercondylar notch 22 of the femur 20, ultimately attaching to the medial and back part of the lateral condyle of the femur 20 at the femoral insertion site 24.

Partial or complete tears of the ACL are very common, with 30,000 new ligament injuries each year from skiing alone. The preferred treatment of the torn ACL is ligament reconstruction, using a bone-ligament-bone autograft. Cruciate ligament reconstruction has the advantage of immediate stability and a potential for immediate vigorous rehabilitation. However, the disadvantages to ACL reconstruction are significant: for example, normal anatomy is disrupted when the patellar tendon or hamstring tendons are used for the reconstruction; placement of intraarticular hardware is required for ligament fixation; and anterior knee pain frequently occurs. Moreover, recent reviews of cruciate ligament reconstruction indicate an increased risk of degenerative arthritis with intraarticular ACL reconstruction in large groups of patients.

A second method of treating ACL injuries, referred to as "primary repair", involves suturing the torn structure back into place. Primary ACL repair has the potential advantages of a limited arthroscopic approach, minimal disruption of normal anatomy, and an out-patient procedure under a local anesthetic. The potential disadvantage of primary cruciate ligament repair is the perception, as indicated below, that over the long term ACL repairs do not provide stability in a sufficient number of patients, and that subsequent reconstruction may be required at a later date. The success rate of anterior cruciate ligament repair has generally hovered in the 60% to 70% range.

Cruciate ligament repairs were initially documented by William H. Battle in 1898 in *Transactions of the Clinical Society of London*, Dec. 13, 1898, vol.XXXIII pg. 232. There was a subsequent larger report by Mayo Robson in 1902, (Mayo, A. W.; Ruptured crucial ligaments and their repair by operation. Read at the Clinical Society of London, December, 1902) when he used cat gut ligatures and sutured the ligament to the synovial membrane and tissues in the inner side of the external condyle. The post-operative regimen prescribed by Robson in 1902, including plaster of paris which was not removed for a month, followed by exercises with a massage therapist, did not change significantly until the early 1970's. Subsequent authors documenting repairs included the papers of Palmer, 1938, O'Donahue, 1973, and Erikkson, 1976 (Palmer, J. On injuries to the ligaments of the knee joint. A clinical study. Acta. Chir. Scand. Suppl. 53, 1938. Eriksson, E.: Sports injuries of the knee ligament: Their diagnosis, treatment, rehabilitation, and prevention. Med Sci Sports. 8:133–144, 1976. O'Donoghue, D., Frank, G. R., et al: Repair and reconstruction of the anterior cruciate ligament in dogs. J. Bone Joint Surg 53A:710–718, 1971). Most authors however refer to Marshall's work at the Hospital for Special Surgery in New York in the 1970's, in which cruciate ligament deficient knees were repaired with figure of 8 suture placement followed by cast treatment (Marshall, J. L., Warren, R. F., Wickiewicz, T. L., Reider, B. The anterior cruciate ligament. A technique of repair and reconstruction. Clin Orthop 143:97–106, 1979.) Marshall reported 75% return to all pre-injury sports activities in his initial follow up at 29 months. A subsequent study by Gollehon in 1985 noted deterioration of these results over time (Gollehon, D. L., Warren, R. F., Wickiewicz, T. L.: Acute repairs of the anterior cruciate ligament—Past and present. Orthop Clin North Am 16:111–124, 1985.).

Feagin, J. A. (1979) *Orthop. Clin. North Am* 10, 81, and Feagin, J. A. et al. (1976) *Am. J. Sports Med.* 4, 95, reported a five year follow up study of 32 torn ACLs repaired primarily with a figure of 8 suture brought through drill holes in the femoral condyle and tied over the bone. The postoperative program was again cast treatment. They noted that their initial good results of 83% of patients achieving stability had deteriorated after five years, with 94% of patients noting instability. Based on these findings, in 1982, Feagin recommended ligament augmentation using the iliotibial band and abandoned primary repair alone.

Higgins, R. W. and Steadman, J. R. (1987) *Am. J. Sports Med.* 15, 439–447, reported results of surgical repair of cruciate ligament with a more modern technique and a more modern postoperative rehabilitation program. Multiple sutures were again placed through an open surgical procedure and reinforced with a lateral iliotibial band tenodesis. Only high level competitive athletes were chosen. The relative contribution of the ligament repair and the lateral iliotibial band tenodesis could not be determined. The joint, rather than undergoing cast treatment, was mobilized after surgery. Additionally, post-operatively the patients underwent immediate rehabilitation exercises.

Sherman, M. F., et al. (1991) *Am. J. Sports Med.* 19, 243–255, analyzed fifty repairs using the Marshall technique. However, only 38% were isolated tears to the ligament, 62% having associated significant injuries. Sherman et al. noted that 77% of the outcomes of ACL repair in this study were good to excellent and that increasing age, tight jointedness, type I tears, and a 5 degree flexion contracture were specifically found to be correlated with good post-operative results.

Kaplan, N., et al. (1990) *Am. J. Sports Med.* 18, 354–358, again reviewed Marshall's original patients with a follow up average of 82 months. Stability testing revealed an 82% clinical examination success rate with a 58% KT 1000 arthrometer success rate at less than 3 mm of side to side difference in a 20 pound pull.

Straub, T., et al. (1988) *Clin. Orth. and Related Research* 227, 238–250, reviewed 66 consecutive patients who underwent acute repairs. Straub et al. defined the term "isolated ACL rupture" as referring to ACL disruption without accompanying grade III medial lateral or posterior lateral laxity. This study included patients with meniscal tears or minor damage to other ligamentous and capsular structures, rated as grade II laxity. Surgical technique was referred to as a modified Marshall technique using multiple loop Tevdek (Deknatel, Queens Village, N.Y.) sutures passed through a drill hole in the lateral femoral condyle. Iliotibial band augmentation, however, was added. The patients were treated with cast immobilization for six weeks at 45 degrees of flexion. Although physical examination follow up was completed in only 76% of the patients, the subjective results were good or better in 91% of these patients. Clinical stability was noted in 88%, and by arthrometer testing, 87% of the patients.

Sommerlath, K., et al. (1991) *Am. Journal of Sports Med.* 19, 156–162, evaluated 53 patients with a nine to sixteen year follow up of cruciate ligament repair. Although all ligaments were repaired using sutures, there was no effort at classifying proximal, mid, or distal ruptures. Most meniscal tears were removed rather than repaired. The post-operative program consisted of casting for four to six weeks without weight bearing. These authors noted a 64% positive Lachman's sign (subjective measurement of anterior excursion of tibia relative to femur with knee flexed at 30°) and a 40% positive pivot shift, a manual testing maneuver that cannot be performed in the presence of an intact anterior cruciate ligament A frequently cited reason for failure of cruciate ligament repair is that, "The synovial fluid is inhibitory to the healing environment". This concept however is not supported by basic science research evaluating the healing ability of the cruciate ligament. Specifically, Lazovic, D. et al. (1993) *Acta Orthop. Scand.* 64, 583–586, reviewed cruciate ligament repair in ruptured dog ligaments. These investigators noted that in trying to evaluate whether a fibrin adhesive would help improve ligament healing. The evaluated ligaments were after acute rupture, followed by repair with Dexon sutures and external fixture immobilization for 3, 6, or 12 weeks, demonstrated organized collagen tissue, interspersed with vascularized unorganized collagen repair tissue for cellular tissue and extra ligamentous vascular connective tissue of synovial character overlying the ligament. All ligaments healed macroscopically. The percentage of organized collagen tissue was around 20% at 3 weeks and tended to increase over time, where 70% of the ligament had normal collagenous structure at 12 weeks. Clearly the synovial environment permitted a healing repair process. Normal collagenous tissue at 12 weeks however, did not have a normal collagen alignment. There was significant variation in tissue distribution within the treatment groups, as has been noted by Amiel, D., et al. (1989) *Journal Orthop. Res.* 7, 486–493. Disruption of the cruciate ligament leads to disorganization of ACL structure with degeneration and loss of cellularity and matrix in the short term. End to end adaption of the transected ligament seemed to initiate the healing process with progressive increase in organization of the collagen tissue over time. Unrepaired and unopposed ACLs tend to lead to atrophy and disfunction, as noted by Kohn, D. (1986) *Arthroscopy* 2, 98–102.

A need remains, therefore, for improved methods for effecting repair of ACL injuries.

SUMMARY OF THE INVENTION

The present inventor has devised an arthroscopic ACL repair method which uses suture anchors. In accordance with the method of the invention, the torn ACL is re-attached to the anatomic insertion site on the femoral condyle using a suture anchor, after a bloody healing bed has been created at or near the attachment site of the cruciate ligament.

In one embodiment, the invention provides a method of repairing a rupture in an anterior cruciate ligament of a knee, said ruptured ligament having a tibial portion extending from an insertion site on the tibia of said knee to a tibial distal tip, and said ligament further having a femoral portion extending from an insertion site on the femoral intercondylar notch of said knee to a femoral distal tip, comprising steps of: establishing an access portal in said knee to expose said ligament and said notch; creating a bleeding bed within cancellous bone located in a portion of said notch corresponding substantially to said insertion site thereon; passing one or more sutures through a region of said tibial portion near said tibial distal tip; affixing a suture anchor to said notch at said bleeding bed, and attaching said sutures to said suture anchor, wherein said tibial distal tip is operatively coupled to said insertion site of said notch. The steps of passing the sutures through the tibial portion, affixing the suture anchor to the notch, and attaching the sutures to the suture anchor may be performed in any order.

BRIEF DESCRIPTION OF THE DRAWINGS

The various features of the invention may be more fully understood from the following description when read together with the accompanying drawings.

DETAILED DESCRIPTION OF THE PREFERRED EMBODIMENT

Figure 1:
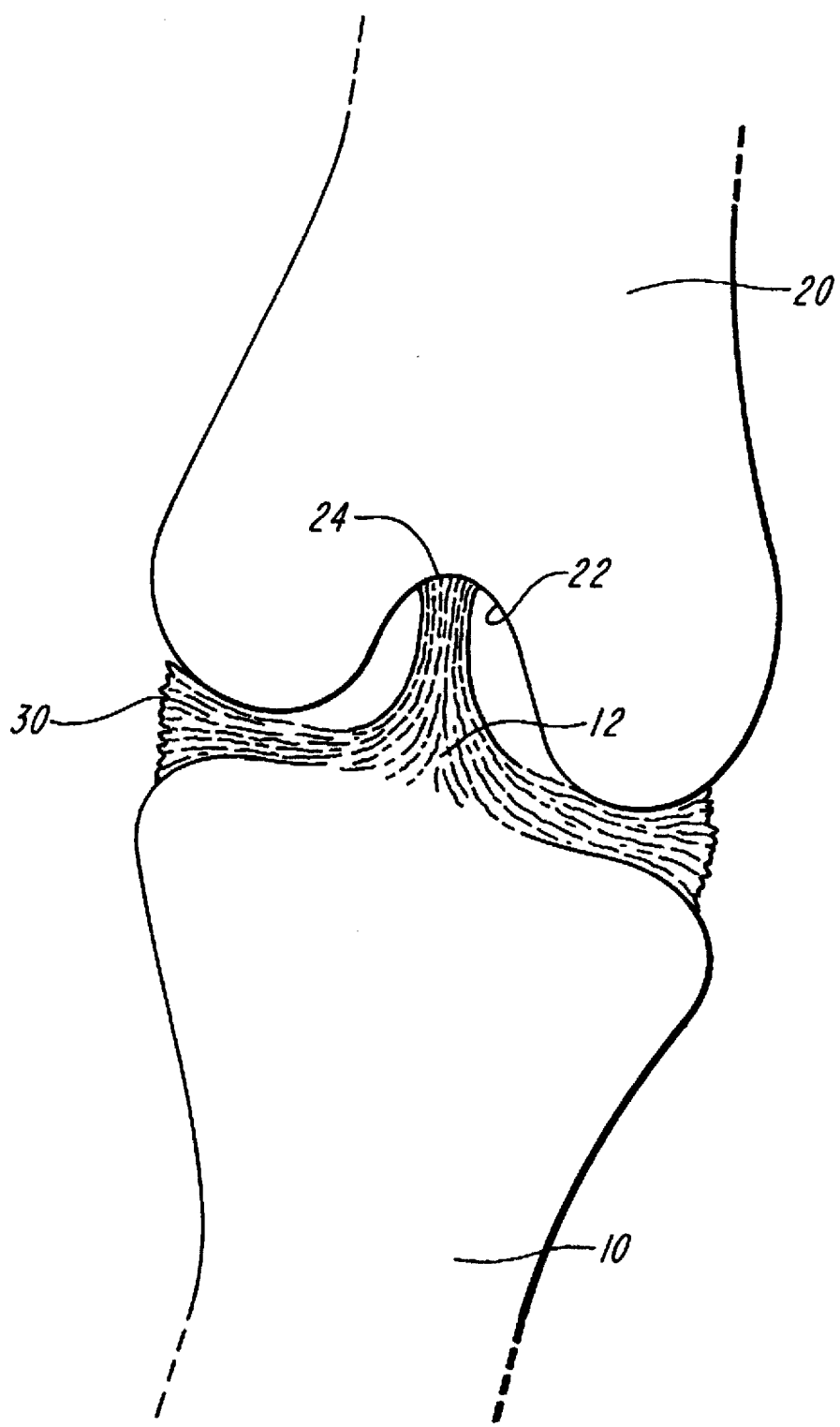
FIG. 1 is a schematic depiction of an intact ACL.
Figure 2:
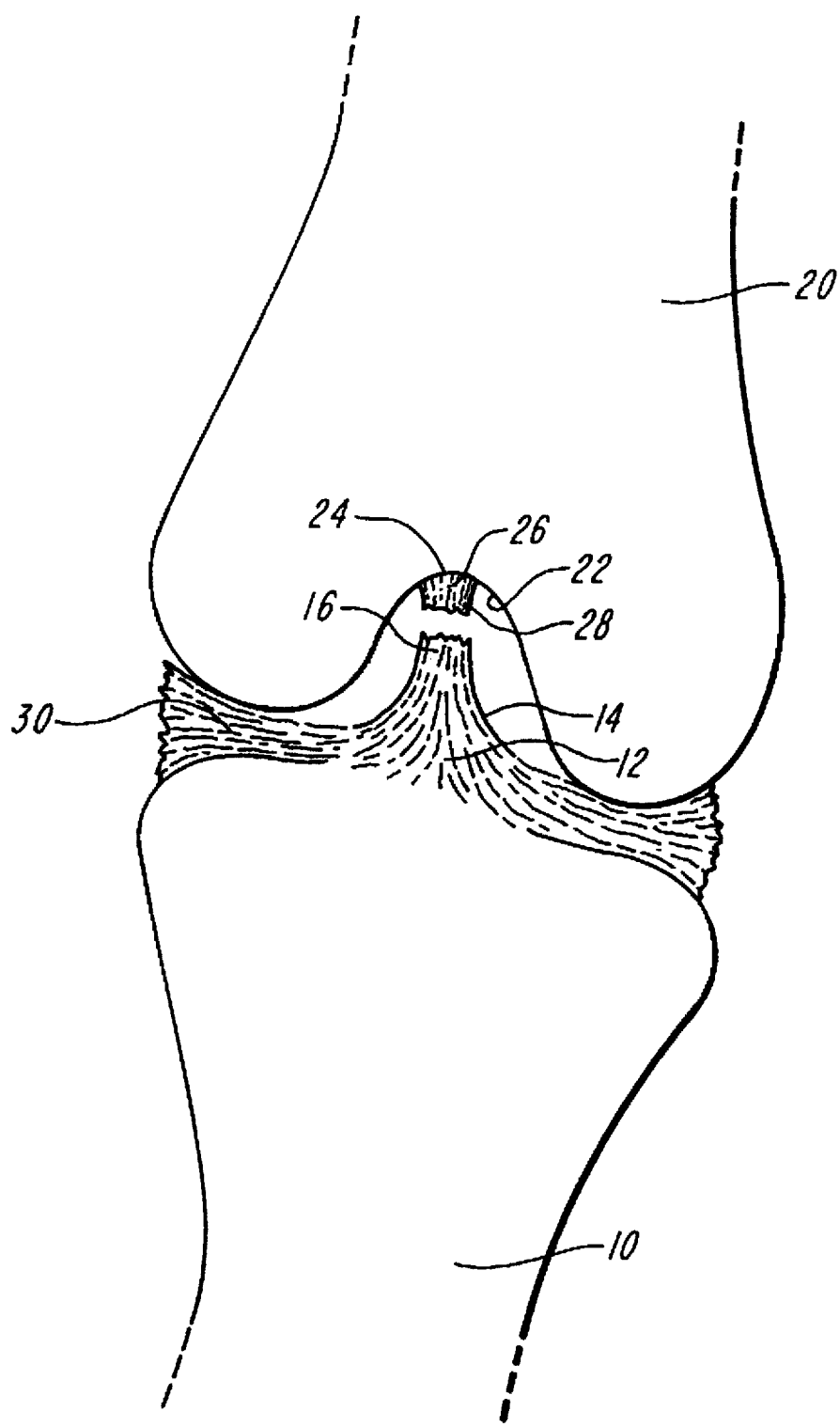
FIG. 2 is a schematic depiction of a ruptured ACL.

Tears or ruptures of the ACL may divided into three groups. The first group (hereinafter Type I ACL tears) are proximal tears of the ACL in which the ligament itself is not displaced significantly anterior to the posterior cruciate ligament, but in which the ACL is disrupted from the femoral wall. Type II ACL tears are those ruptures that are predominantly proximal, but which are easily displaceable anterior to the posterior cruciate ligament, often including fibers disrupted into the joint or obstructing the joint motion. Type III ACL tears are ruptures involving gross comminution of the ACL proximally and centrally or distally. Type III ACL tears are preferably treated by ACL reconstruction. Type I and II ACL tears are preferably repaired using the method of the invention. As schematically depicted in FIG. 2, the ruptured ligament comprises a tibial portion 14 which extends from the insertion site 12 of the ACL on the tibia 10 to a tibial distal tip 16 and a femoral portion 26 which extends from the insertion site 24 of the ACL on the femoral intercondylar notch 22 to a femoral distal tip 28. The method of the present invention is particularly useful for repairing ACLs which are torn at the proximal portion (posterior in the intercondylar notch).

In accordance with the method of the invention, ACL repairs are preferably performed soon after occurrence of the injury, most preferably within two weeks of injury. Generally, in the method of the invention, the patient's leg is placed in a standard leg holder with the knee flexed over the end of the operating table. After anesthetizing the knee, several portals are made in the knee. Preferably, several portal incisions are made at different positions on the knee so that different instruments may be inserted at different sites on the knee. Placement of such portals is determined by the arthroscopic surgeon. A visualization portal is made for insertion of the arthroscope, which is used to assess the extent of injury to the ACL and to visualize the progress of the method of the invention. Visualization of the site of the rupture and access to the insertion site of the ACL on the femoral intercondylar notch may optionally be improved by molding or shaping the anterior portion of the notch, using, e.g., an arthroscopic shaver ("anterior notchplasty"). If this step is performed, the anterior aspect of the femoral intercondylar notch is debrided, but the posterior aspect of the notch, where the ACL insertion site is located, is not debrided. If no notchplasty is performed, an access portal is made through which the method of the invention is performed.

In accordance with the invention, a bleeding bed is created within the cancellous bone (substantia spongiosa) corresponding substantially to the anatomic insertion site 24 of the ACL on the femoral intercondylar notch, by producing a plurality of microfractures in the posterior aspect of the notch. "Corresponds substantially" is defined herein to mean ranging from one to ten millimeters anterior to the posterior cortex of the medial wall of the lateral femoral condyle and extending, from the twelve to the four o'clock position. The microfractures may be produced using surgical tools known as microfracture awls or picks, which are commercially available, for example, from Linvatec, Inc. (Largo, Fla.). The microfracture awls are inserted through the access portal, and placed in such a way that the microfractures will correspond substantially to the ACL insertion site 24. Pressure is applied to the exposed ends of the microfracture awls, through a series of impacts using a mallet, for example, to create the microfractures. Preferably, the microfractures are 5–10 mm deep with an inter-hole spacing in the range 1–5 mm and preferably 2–3 mm. Any number of microfractures may be produced to form the bleeding bed. Preferably, five to fifteen microfractures are produced to form the bleeding bed. More preferably, five to ten microfractures are produced to form the bleeding bed.

When the tibial distal tip 16 of the ruptured ligament is rounded off by natural resorption, the ligament itself may also be microfractured to create a rough surface on the tibial distal tip 16 thereby increasing blood clot formation and enhancing coupling between the tibial distal tip 16 and the ACL insertion site 24 on the femoral intercondylar notch.

Figure 3:
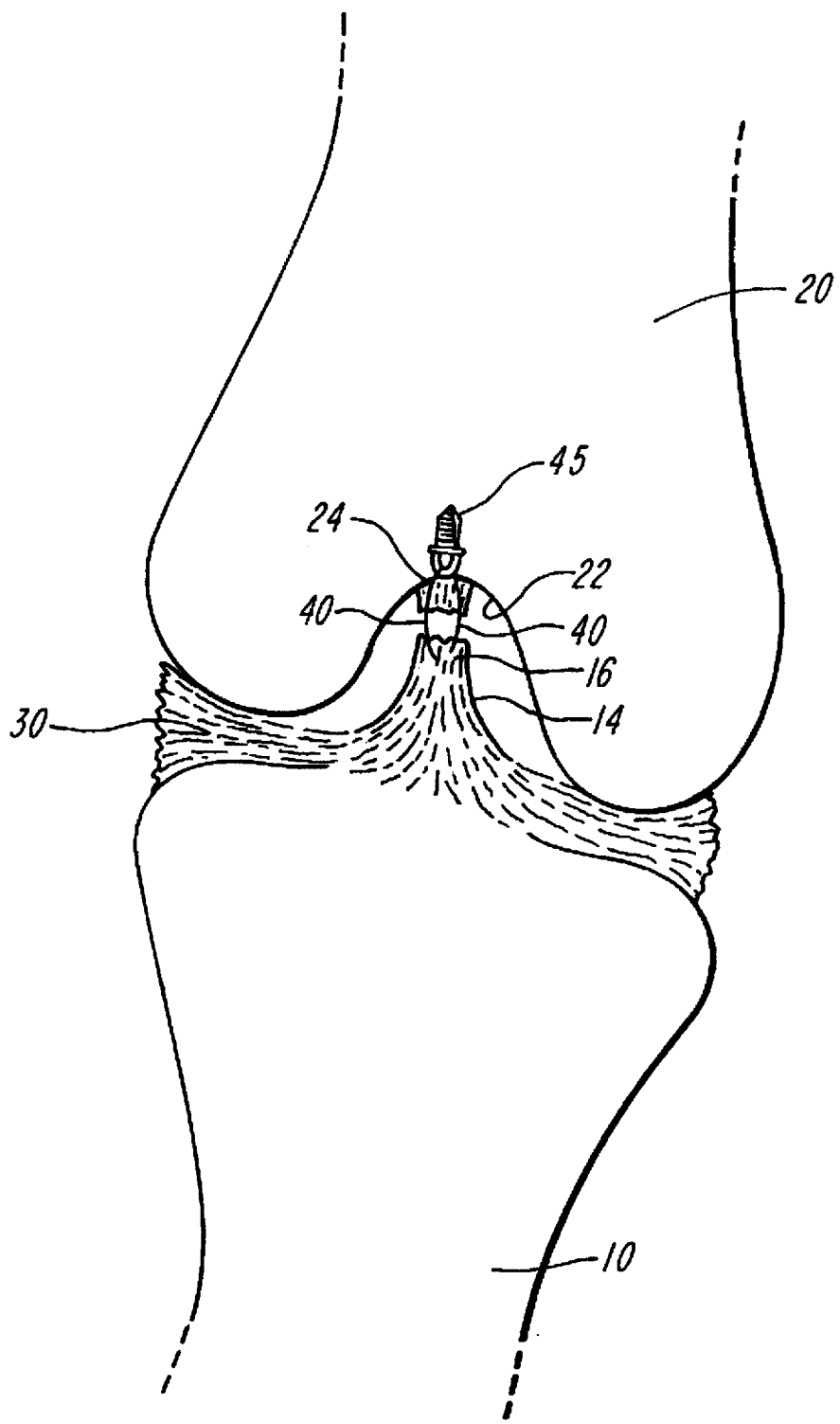
FIG. 3 is a schematic depiction of a ruptured ACL which has been repaired using the method of the invention.

As is schematically depicted in FIG. 3, coupling between the tibial distal tip 16 and the ACL insertion site 24 on the femoral intercondylar notch 22 is accomplished in accordance with the invention using one or more sutures 40 which are passed through a region of the tibial portion 14 of the ruptured ligament near the tibial distal tip 16, and a suture anchor 45 affixed to the femoral intercondylar notch 22 at the site of the bleeding bed (corresponding substantially to 24). The sutures 40 are attached to the suture anchor 45 in such a way that tension is applied to the sutures 40 to bring the tibial distal tip 16 into spatial proximity to the bleeding bed, and thus to the insertion site 24 of the ACL in the femoral intercondylar notch 22. As defined herein, the tibial distal tip 16 of the ruptured ligament is "operatively coupled" to the ACL insertion site 24 on the femoral intercondylar notch 22 when it is held in spatial proximity to the bleeding bed and thus to the insertion site 24 such that in the course of healing, tissue forms between the tibial distal tip 16 and the ACL insertion site 24.

In accordance with the invention, the steps of passing the sutures through the region of the tibial portion of the ruptured ligament near the tibial distal tip, affixing the suture anchor to the femoral intercondylar notch at the site of the bleeding bed, and attaching the sutures to the suture anchor may be performed in any order. For example, in one embodiment the sutures are first attached to the suture anchor, and secondly the suture anchor is affixed to the femoral intercondylar notch at the site of the bleeding bed, and thirdly the sutures are passed through the tibial distal tip. Alternatively, the suture anchor is first affixed to the femoral intercondylar notch at the site of the bleeding bed, and secondly the sutures are attached to the suture anchor, and thirdly the sutures are passed through the tibial distal tip. In another embodiment, the sutures are first passed through the tibial distal tip, and secondly the suture anchor is affixed to the femoral intercondylar notch at the site of the bleeding bed, and thirdly the sutures are attached to the suture anchor. In yet another embodiment, the sutures are first passed through the tibial distal tip, secondly the sutures are attached to the suture anchor, and thirdly the suture anchor is affixed to the femoral intercondylar notch at the site of the bleeding bed.

In accordance with the invention, one or more sutures are passed through the ruptured ligament in a region near the tibial distal tip. The attending physician will determine the number of sutures required to accomplish the method of the invention, in light of his or her assessment of the extent of injury, the patient's condition and the patient's prior history. Such determinations are well within the level of skill of orthopedic surgeons. Prior to the step of passing the suture or sutures through the ruptured ligament, one or more holes may optionally be established in the region near the tibial distal tip of the ruptured ligament, to facilitate passage of the sutures therethrough.

Any suture anchor may be used to practice the method of the invention. For example, the suture anchor may be of the type disclosed in U.S. Pat. No. 5,370,662, which has a self-drilling, tapping leading end and a trailing end. Alternatively, the suture anchor may be of the type disclosed in U.S. Pat. No. 4,632,100, which has a self-tapping leading end and a trailing end. Suture anchors which are implanted by one or more impacts, applied to the external portion of the cannulated driver by a mallet may also be used in the method of the invention. Suture anchors which permit multiple sutures to be loaded on each anchor are preferred. The suture anchors are preferably removably coupled to an associated cannulated driver.

When a self-drilling, self-tapping suture anchor is used, the leading end of the suture anchor is biased against a point on the femoral intercondylar notch corresponding substantially to the insertion site of the ACL. The cannulated driver and coupled suture anchor are rotated, whereby the leading end of the suture anchor simultaneously drills and taps into the femoral intercondylar notch, thereby accomplishing the affixation step of the method of the invention. The driver is then decoupled from the suture anchor and removed from the joint.

When a suture anchor of the type disclosed in U.S. Pat. No. 4,632,100 is used, a hole is first drilled into the joint at a position within the bleeding bed and thus corresponding substantially to the insertion site of the ACL in the femoral intercondylar notch, using a suture anchor drill. The drill is removed, and the leading end of the suture anchor, on the arthroscopic driver, is then inserted into the drill hole. The cannulated driver and coupled suture anchor are rotated, whereby the leading end of the suture anchor taps into the femoral intercondylar notch, thereby accomplishing the affixation step of the method of the invention. The driver is then decoupled from the suture anchor and removed from the joint.

The following example illustrates the preferred mode of practicing the present invention, but are not meant to limit the scope of the invention since alternative methods may be used to obtain similar results.

EXAMPLE

Fifty patients underwent ACL repair by either the technique of the invention or by using only microfracture of the posterior intercondylar notch to create a healing response. Pre-operatively all patients filled out a questionnaire, underwent an arthroscopic examination by an experienced nurse practitioner, physical examination by the orthopedic surgeon, x-ray, and magnetic resonance imaging (MRI) examination. The MRI protocols included an axial locator scan, sagittal fat suppression sequence, coronal fat suppression sequence, axial fat suppression sequence, and also fast spin echo on the axial, coronal, and sagital views.

Surgical technique for primary repair included complete diagnostic arthroscopic evaluation of all joint compartments through the visualization portal, followed by repair of meniscal tears, and treatment of any other articular cartilage lesions. Next, the injury to the ACL was carefully assessed and typed according to the criteria set forth above.

Type I and II ACL tears were treated by the following technique. Initially an anterior notchplasty was performed. Then, five to ten microfractures were produced as set forth above to create a bleeding bed in the cancellous bone at the site of ACL insertion on the femoral intercondylar notch. After the intercondylar notch preparation was performed, an oval obturator was inserted through the access portal. Two suture punches were then loaded with two different color #1 monofilament sutures of nylon and polydixone (PDS, Ethicon.). The suture punches were then inserted through the access portal and punctured through the ligament sequentially from the mid aspect to the proximal aspect of the ligament. The sutures were then carried out through the access portal. A hole was then manually drilled into the 11 o'clock position on the intercondylar notch using a suture anchor drill. The drill was removed with pliers. The two monofilament sutures were then threaded through a suture anchor of the type disclosed in U.S. Pat No. 4,632,100, after it was placed on the arthroscopic driver. The suture anchor, on its cannulated driver, was then advanced through the portal and inserted into the drill hole with a mallet. The driver was removed from the joint.

The free ends of the suture were then tied with a fisherman's slip knot and advanced into the joint securing the ACL to the suture anchor and bone. At the completion of the knot tying for each of the three sutures, arthroscopic scissors were used to trim the remaining suture ends. The knee was then taken through a full range of motion to assure that there was no impingement and that the ligament was securely fixed to the anatomic insertion site on the femoral intercondylar notch.

After surgery the knee was placed in a post-operative knee brace, blocked from 30 degrees to 80 degrees of flexion. Full weight bearing was permitted and the patients were encouraged to initiate immediate single stance and double stance knee bends in the fully weighted position. The knee bends were performed for three sets of three minutes on each leg twice a day. Balance exercises using a balance board were initiated on day one after surgery and continued throughout the rehabilitation program. Hip adduction/abduction exercises, and calf exercises with ankle foot pumps were performed daily. At four weeks, the knee brace was discontinued and active full range of motion initiated, both passively and actively. Bicycling rehabilitation exercises were started, as well as full functional rehabilitation exercises. At three months, sports specific drills were begun and return to sports was permitted, based on muscle strength tests, and the ability to pass a balance and proprioception test Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. A method of repairing a rupture in an anterior cruciate ligament of a knee, said ruptured ligament having a tibial portion extending from an insertion site on the tibia of said knee to a tibial distal tip, and said ligament further having a femoral portion extending from an insertion site on the femoral intercondylar notch of said knee to a femoral distal tip, comprising steps of:

A. establishing an access portal in said knee to expose said ligament and said notch, B. creating a bleeding bed within cancellous bone located in a portion of said notch corresponding substantially to said insertion site thereon, C. passing one or more sutures through a region of said tibial portion near said tibial distal tip, D. affixing a suture anchor to said notch at said bleeding bed, and E. attaching said sutures to said suture anchor, wherein said tibial distal tip is operatively coupled to said insertion site of said notch.

2. The method according to claim 1 including the further step of:

prior to step B, performing anterior notchplasty at said notch to establish increased access to said insertion site on said notch.

3. The method according to claim 1 including the further step of:

prior to step C, establishing one or more holes in said tibial portion near said tibial distal tip to permit passage of one or more sutures therethrough.

4. The method according to claim 1, wherein said steps C, D, and E are performed in the sequential order E, D, C.

5. The method according to claim 4 wherein said suture anchor affixing step D includes the substeps of:

i. drilling a hole in said bleeding bed, ii. providing said anchor and an associated cannulated driver, said anchor having a self-tapping leading end and having a trailing end, said anchor being removably coupled to said driver, iii. inserting said leading end of said anchor in said hole, iv. rotating said driver and coupled anchor, whereby said leading end is driven into said hole, thereby affixing said anchor to said notch, and v. decoupling said driver from said anchor and removing said driver.

6. The method according to claim 4 wherein said suture anchor attaching step D includes the substeps of:

i. providing said anchor and an associated cannulated driver, said anchor having a self-drilling, self-tapping leading end and having a trailing end, said anchor further being removably coupled to said driver, ii. biasing said leading end against a point on said notch substantially at said insertion site, iii. rotating said driver and coupled anchor, whereby said leading end drills into said notch, thereby affixing said anchor to said notch, and iv. decoupling said driver from said anchor and removing said driver.

7. The method according to claim 1, wherein said steps C, D, and E are performed in the sequential order D, E, C.

8. The method according to claim 7 wherein said suture anchor affixing step D includes the substeps of:
   i. drilling a hole in said bleeding bed,
   ii. providing said anchor and an associated cannulated driver, said anchor having a self-tapping leading end and having a trailing end, said anchor being removably coupled to said driver,
   iii. inserting said leading end of said anchor in said hole,
   iv. rotating said driver and coupled anchor, whereby said leading end is driven into said hole, thereby affixing said anchor to said notch, and
   v. decoupling said driver from said anchor and removing said driver.

9. The method according to claim 7 wherein said suture anchor attaching step D includes the substeps of:
   i. providing said anchor and an associated cannulated driver, said anchor having a self-drilling, self-tapping leading end and having a trailing end, said anchor further being removably coupled to said driver,
   ii. biasing said leading end against a point on said notch substantially at said insertion site,
   iii. rotating said driver and coupled anchor, whereby said leading end drills into said notch, thereby affixing said anchor to said notch, and
   iv. decoupling said driver from said anchor and removing said driver.

10. The method according to claim 1, wherein said steps C, D, and E are performed in the sequential order C, D, E.

11. The method according to claim 10 wherein said suture anchor affixing step D includes the substeps of:
    i. drilling a hole in said bleeding bed,
    ii. providing said anchor and an associated cannulated driver, said anchor having a self-tapping leading end and having a trailing end, said anchor being removably coupled to said driver,
    iii. inserting said leading end of said anchor in said hole,
    iv. rotating said driver and coupled anchor, whereby said leading end is driven into said hole, thereby affixing said anchor to said notch, and
    v. decoupling said driver from said anchor and removing said driver.

12. The method according to claim 10 wherein said suture anchor attaching step D includes the substeps of:
    i. providing said anchor and an associated cannulated driver, said anchor having a self-drilling, self-tapping leading end and having a trailing end, said anchor further being removably coupled to said driver,
    ii. biasing said leading end against a point on said notch substantially at said insertion site,
    iii. rotating said driver and coupled anchor, whereby said leading end drills into said notch, thereby affixing said anchor to said notch, and
    iv. decoupling said driver from said anchor and removing said driver.

13. The method according to claim 1, wherein said steps C, D, and E are performed in the sequential order C, E, D.

14. The method according to claim 13 wherein said suture anchor affixing step D includes the substeps of:
    i. drilling a hole in said bleeding bed,
    ii. providing said anchor and an associated cannulated driver, said anchor having a self-tapping leading end and having a trailing end, said anchor being removably coupled to said driver,
    iii. inserting said leading end of said anchor in said hole,
    iv. rotating said driver and coupled anchor, whereby said leading end is driven into said hole, thereby affixing said anchor to said notch, and
    v. decoupling said driver from said anchor and removing said driver.

15. The method according to claim 14 wherein said suture anchor attaching step D includes the substeps of:
    i. providing said anchor and an associated cannulated driver, said anchor having a self-drilling, self-tapping leading end and having a trailing end, said anchor further being removably coupled to said driver,
    ii. biasing said leading end against a point on said notch substantially at said insertion site,
    iii. rotating said driver and coupled anchor, whereby said leading end drills into said notch, thereby affixing said anchor to said notch, and
    iv. decoupling said driver from said anchor and removing said driver.

* * * * *